(12) United States Patent
Turchi et al.

(10) Patent No.: US 9,730,942 B2
(45) Date of Patent: Aug. 15, 2017

(54) MATERIALS AND METHOD FOR INHIBITING REPLICATION PROTEIN A AND USES THEREOF

(71) Applicant: Indiana University Research and Technology Corporation, Indianapolis, IN (US)

(72) Inventors: John J. Turchi, Indianapolis, IN (US); Sarah Shuck, Nashville, TN (US)

(73) Assignee: Indiana University Research and Technology Corporation, Indianapolis, IN (US)

( * ) Notice: Subject to any disclaimer, the term of this patent is extended or adjusted under 35 U.S.C. 154(b) by 0 days.

(21) Appl. No.: 15/396,978

(22) Filed: Jan. 3, 2017

(65) Prior Publication Data

US 2017/0182055 A1 Jun. 29, 2017

Related U.S. Application Data

(60) Continuation of application No. 14/470,585, filed on Aug. 27, 2014, now Pat. No. 9,533,969, which is a division of application No. 13/576,023, filed as application No. PCT/US2011/023838 on Feb. 5, 2011, now Pat. No. 8,859,532.

(60) Provisional application No. 61/301,778, filed on Feb. 5, 2010.

(51) Int. Cl.
| | | |
|---|---|---|
| *A01N 43/00* | (2006.01) | |
| *A61K 31/33* | (2006.01) | |
| *A61K 31/5377* | (2006.01) | |
| *A61K 31/4709* | (2006.01) | |
| *A61K 9/00* | (2006.01) | |
| *A61K 47/38* | (2006.01) | |
| *A61K 47/26* | (2006.01) | |
| *A61K 45/06* | (2006.01) | |

(52) U.S. Cl.
CPC ........ *A61K 31/5377* (2013.01); *A61K 9/0053* (2013.01); *A61K 31/4709* (2013.01); *A61K 45/06* (2013.01); *A61K 47/26* (2013.01); *A61K 47/38* (2013.01)

(58) Field of Classification Search
None
See application file for complete search history.

(56) References Cited

FOREIGN PATENT DOCUMENTS

| WO | WO 2007/120842 | 10/2007 |
| WO | WO 2008/045663 | 4/2008 |
| WO | WO 2009/145829 | 12/2009 |

OTHER PUBLICATIONS

Patrick SM, Turchi JJ. "Replication Protein A (RPA) Binding to Duplex Cisplatin-damaged DNA is Mediated through the Generation of Single-stranded DNA," J. Biol. Chem., 1999, 274, 14972-14978.
Patrick SM, Turchi JJ, "Stopped-flow kinetic analysis of replication protein A-binding DNA—Damage recognition and affinity for single-stranded DNA reveal differential contributions of k(on) and k(off) rate constants," J. Biol. Chem., 2001, 276.22630-22637.
Turchi J. et al., "Targeting Nucleotide Excision Repair as a Mechanism to Increase Cisplatain Efficacy," In: Bonetti A, Leone R, Muggia FM, Howell SB, editors. Platinum and Other Heavy Metal Compounds in Cancer Chemotherapy. New York: Humana Press; 2009, 177-187, published Dec. 18, 2008.
Wold MS, "Replication protein A: a heterotrimeric, single-stranded DNA—binding protein required for eukaryotic DNA metabolism," Annual Review of Biochemistry, 1997, 66, 61-92.
Shuck, S. et al., "Abstract #5545: The effect of a small molecule inhibitor of Replication Protein A (TDRL-505) on DNA binding, cellular function and platinum sensitivity." Cancer Research, May 1, 2009, 69, 5545.
Vidal. D. et al., "Structure-based discovery of new small molecule inhibitors of low molecular weight protein tyrosine phosphatase," European Journal of Medicinal Chemistry, 2007, 42, 1102-1108.
CAS RN: 131645-11-9 (entered Jan. 25, 1991).
Granadillo, V.J.A., et al., "Targeting the OB-Folds of Replication Protein A with Small Molecules," Journal of Nucleic Acid. 2010, 1-11, 2010. 2010.
European Search Opinion for Pat. App. 11740474.9, European Patent Office, dated Aug. 5, 2013, pp. 1-5.
PubChem CID 3153480, 4-(3,5-diphenyl-3, 4-dihydropyrazol-2-yl)-4-oxobutanoic acid 4-(3, 5-Diphenyl-4, 5-dihydro-pyrazol-1-yl)-4-oxo-butyric acid <available at hhtp ://pubchem.nc bi.nlm.nih. gov/ summary/ summary .chi? cid= 315 3480&loc=ec __res.
Andrews, "Development of a high-throughput screen for inhibitors of replication protein A and its role in nucleotide excision repair," Mol. Cancer Ther., 2004, 3, 385-391.
Deng, "Structure of the Full-length Human RPA 14/32 Complex Gives Insights into the Mechanism of DNA Binding and Complex Formation," J. Mol. Biol., 2007, 374, 865-876.
Sharp, "In vitro Biological Characterization of a Novel, Synthetic Inhibitors Diaryl Pyrazole Resorcinol Class of Heat Shock Protein 90," Cancer Res., 2007, 67, 2206-2216.
Shuck, "Identification of Novel Small Molecule Inhibitors of Proteins Required for Genomic Maintenance and Stability," Doctoral thesis, Indiana University. Jun. 2010, pp. 1-131 <available at https://scholar works .iupui.edu/bitstream/handle/ 1805/223 3/Final%20thesis%2003.pdf?sequence=1 >.

(Continued)

*Primary Examiner* — Jared D Barsky
(74) *Attorney, Agent, or Firm* — Barnes & Thornburg LLP

(57) ABSTRACT

Targeting uncontrolled cell proliferation and resistance to DNA damaging chemotherapeutics with at least one reagent has significant potential in cancer treatment. Replication Protein A, the eukaryotic single-strand (ss) DNA binding protein, is essential for genomic maintenance and stability via roles in both DNA replication and repair. Reported herein are small molecules that inhibits the in vitro, in vivo, and cellular ssDNA binding activity of RPA, thereby disrupting the eukaryotic cell cycle, inducing cytotoxicity and increasing the efficacy of chemotherapeutic agents damage DNA, and/or disrupt its replication and/or function. These results provide new insights into the mechanism of RPA-ssDNA interactions in chromosome maintenance and stability. This represents a molecularly targeted eukaryotic DNA binding inhibitor and demonstrates the utility of targeting a protein-DNA interaction as a means of studying the cell cycle and providing a therapeutic strategy for cancer treatment.

20 Claims, 17 Drawing Sheets

(56) References Cited

OTHER PUBLICATIONS

International Search Report of the International Searching Authority for PCT/US2011/023838, dated May 2011.
The Written Opinion of the International Searching Authority for PCT/US2011/023838, dated May 2011.
The International Preliminary Report on Patentability of the International Searching Authority for PCT/US2011/023838, dated Aug. 2012.
Shuck, S. el al., "Targeted Inhibition of Replication Protein A Reveals Cytotoxic Activity, Synergy with Chemotherapeutic DNA-Damaging Agents, and Insight into Cellular Function," American Association for Cancer Research. 2010, 70, 3189-3198.

(μm)

MATERIALS AND METHOD FOR INHIBITING REPLICATION PROTEIN A AND USES THEREOF

PRIORITY CLAIM

This application is a continuation of U.S. patent application Ser. No. 14/470,585, filed Aug. 27, 2014, which is a divisional of U.S. patent application Ser. No. 13/576,023, filed Oct. 15, 2012, which is a §371 national stage application of International Application Number PCT/US2011/023838, filed Feb. 5, 2011, titled Materials and Methods for Inhibiting Replication Protein A and Uses Thereof, which claims the benefit of U.S. provisional patent application No. 61/301,778 filed on Feb. 5, 2010, and the disclosure of each application is expressly incorporated herein by reference in its entirety.

STATEMENT OF GOVERNMENTAL RIGHTS

This invention was made with government support under CA082741 awarded by the National Institutes of Health. The government has certain rights in the invention.

FIELD OF THE INVENTION

Some aspects of the invention relate to identifying molecules that at least partially inhibit the activity of the Replication Protein A and these molecules can be used to treat hyper-proliferative diseases, including cancer.

BACKGROUND

Replication protein A (RPA) is a heterotrimeric single-stranded DNA (ssDNA) binding protein made up of 70, 34, and 14 kDa subunits (1). The ssDNA binding activity of RPA is required for several DNA metabolic pathways including DNA replication, recombination and repair. High affinity interactions with DNA are sustained by the numerous oligosaccharide/oligonucleotide binding (OB)-folds present on each of the three subunits (2; 3). The DNA binding pocket of a single OB-fold accommodates 3-4 bases of ssDNA (4; 5). The main OB-folds, DNA binding domains A and B (DBD-A and DBD-B) are present in the central region of the p70 subunit and contribute most of the binding energy for RPA-ssDNA interactions (2). Individual OB-folds are compact modular domains populated with hydrophobic and basic amino acids. These structural features make the OB-folds an attractive target for development of small molecule inhibitors (SMIs) of DNA binding activity. Given RPA's central role in cell growth and DNA repair, it is an attractive target for the development of compounds that can interfere with its activity. Some aspects of the instant invention include compounds that interact with RPA and methods of using the same to influence cell growth and death.

SUMMARY

Various aspects of the invention include methods and compounds for reducing the activity of Replication Protein A, effecting eukaryotic cell proliferation, the cell cycle of eukaryotic cells and/or treating cancer by contacting Replication Protein A with a compound such as compound A or a metabolite thereof that includes the following core structure:

In some embodiments eukaryotic cells contacted with a compound or metabolite thereof includes the core structure are further contacted with at least one compound that damage DNA directly or inhibits topoisomerase II. Such compounds include, but are not limited to, Cisplatin, Etoposide, Busulfan, Bendamustine, Carboplatin, Carmustine, Chlorambucil, Cisplatin, Cyclophosphamide, Dacarbazine, Daunorubicin, Decitabine, Doxorubicin, Epirubicin, Etoposide, Idarubicin, Ifosfamide, Irinotecan, Lomustine, Mechlorethamine, Melphalan, Mitomycin C, Mitoxantrone, Oxaliplatin, Temozolomide, Topotecan and the like.

Some aspects of the invention include methods of reducing the activity of a Replication Protein A, comprising the steps of: providing a compound A, wherein the compound A binds to Replication Protein A or is metabolized into a chemical that binds to Replication Protein A, compound have the following formula:

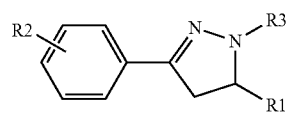

wherein, $R_1$ is selected from the group consisting of: substituted quinolins, thiophenes and phenyls; including 5-(7-chloro-2,3-dihydro-[1,4]dioxino[2,3-g]quinolin-8-yl); 5-(quinoxalin-6-yl); and 6-chloro-[1,3]dioxolo[4,5-g]quinolin-7-yl $R_2$ is selected from the group consisting of: hydrogen, halogens, methyl groups, nitro groups; wherein compound A or a metabolite of compound A binds to Replication Protein A; and $R_3$ is selected from the group consisting of: ketobutyric acids, and

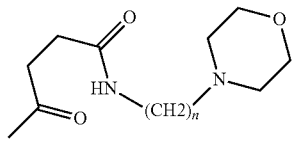

wherein n=1, 2, 3, 4, or 5. In some embodiments the quinolin or the phenyl in compound A is substituted with at least one moiety selected from the group consisting of: halogens, methyl groups, ethyl groups, amino groups and pyrazole. In some embodiments $R_1$ in compound A is selected from the group consisting of: 2-chloro-7-ethoxyquinolin, 5(quinoxalin-6-yl), 2-chloro-6,7-dimethoxyquinolin, 2-chloro-6-ethoxyquinolin, 4-Bromophenyl, 4-fluorophenyl, 4-chlorophenyl, 2-chlorophenyl, 2-methoxyphenyl, 4-ethylphenyl, 4-Diethylaminophenyl, 4-dimethylaminophenyl, Thiophene, 4-methoxyphenyl, p-tolyl, 2,5-dimethoxyphenyl, 3,4-dimethoxyphenyl, 4-ethylphenyl; and 1-phenyl-3-p-tolyl-1H-pryazole; and $R_2$ in compound A is selected from the groups consisting of: 4-bromo, 4-chloro, 4-nitro, 4-methyl, 4-methoxy, H, 3,4-dimethyl.

In some embodiments the molecule that binds to Replication Protein A is a derivative of compound A or a metabolite thereof. And in some embodiments the molecule that binds to Replication Protein A is the compound TDLR-505, the compound TDLR-506, or a metabolite thereof.

In still other embodiments the step of contacting either compound A or a metabolite thereof and the at least one isoform of Replication Protein A occurs in vivo. In still other embodiments the step of contacting compound A or a metabolite thereof and the at least one isoform of Replication Protein A occurs in vitro.

Other aspects of the invention include methods of inhibiting cell proliferation via altering the eukaryotic cell cycle-progression, comprising the steps of: providing a compound A that interferes with eukaryotic cell cycle-progression or that is metabolized into a chemical that interferes with eukaryotic cell cycle-progression, wherein compound A has the following formula:

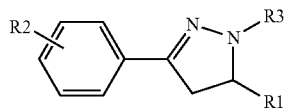

wherein, $R_1$ is selected from the group consisting of: substituted quinolins, thiophenes and phenyls; including 5-(7-chloro-2,3-dihydro-[1,4]dioxino[2,3-g]quinolin-8-yl); 5-(quinoxalin-6-yl); and 6-chloro-[1,3]dioxolo[4,5-g]quinolin-7-yl; $R_2$ is selected from the group consisting of: hydrogen, halogens, methyl groups, nitro groups; wherein compound A or a metabolite of compound A binds to Replication Protein A; and $R_3$ is selected from the group consisting of: ketobutyric acid, and

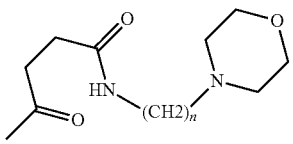

wherein n=1, 2, 3, 4, or 5. In some embodiments the quinolin or the phenyl in compound A is substituted with at least one moiety selected from the group consisting of: halogens, methyl groups, ethyl groups, amino groups and pyrazole. In some embodiments $R_1$ in compound A is selected from the group consisting of: 2-chloro-7-ethoxyquinolin, 5(quinoxalin-6-yl), 2-chloro-6,7-dimethoxyquinolin, 2-chloro-6-ethoxyquinolin, 4-Bromophenyl, 4-fluorophenyl, 4-chlorophenyl, 2-chlorophenyl, 2-methoxyphenyl, 4-ethylphenyl, 4-Diethylaminophenyl, 4-dimethylaminophenyl, Thiophene, 4-methoxyphenyl, p-tolyl, 2,5-dimethoxyphenyl, 3,4-dimethoxyphenyl, 4-ethylphenyl; and 1-phenyl-3-p-tolyl-1H-pryazole; and $R_2$ in compound A is selected from the groups consisting of: 4-bromo, 4-chloro, 4-nitro, 4-methyl, 4-methoxy, H, 3,4-dimethyl.

In some embodiments the compound that at least partially interferes with the eukaryotic cell cycle-progression is the compound A or a metabolite thereof. In still other embodiments the compound that interferes with eukaryotic cell cycle-progression is the compound TDLR-505, TDLR-506, or metabolite thereof. In some embodiments, the contacting step between compound A or a metabolite thereof and the Replication Protein A occurs in vivo.

Still other embodiments include methods for treating human or animal patients comprising the step of supplying or providing at least one therapeutically active amount of at least one compound that inhibits the activity of RPA or a pharmaceutically acceptable salt thereof. Some embodiments include the step of administering a dose of the compound to a patient wherein the dose is about 50 mg of said compound per $kg^{-1}$ of the patient's body weight or about 100 mg of said compound per $kg^{-1}$ of the patient's body weight or about 200 mg of said compound per $kg^{-1}$ of the patient's body weight.

In still other embodiments the contacting step between said compound A or a metabolite thereof and the Replication Protein A occurs in vitro. Still other aspects of the invention include a method treating cancer, comprising the steps of: providing a compound wherein the compound interferes with the cell cycle of a cancer cell or is metabolized into a chemical that interferes with the cell cycle of a cancer cell, and the compound has the formula according to FIG. 2A, in which $R_1$ is selected from the group consisting of: substituted quinolins, thiophenes and phenyls, and $R_2$ in compound A is selected from the group consisting of: halogens, methyl groups, nitro groups; wherein compound A binds to Replication Protein A; and contacting said compound A with at least one cancer cell. In some embodiment the quinolin or the phenyl in compound A is substituted with at least one moiety selected from the group consisting of: halogens, methyl groups, ethyl groups, amino groups and pyrazole. In some embodiments $R_1$ in compound A is selected from the group consisting of: 2-chloro-7-ethoxyquinolin, 5(quinoxalin-6-yl), 2-chloro-6,7-dimethoxyquinolin, 2-chloro-6-ethoxyquinolin, 4-Bromophenyl, 4-fluorophenyl, 4-chlorophenyl, 2-chlorophenyl, 2-methoxyphenyl, 4-ethylphenyl, 4-Diethylaminophenyl, 4-dimethylaminophenyl, Thiophene, 4-methoxyphenyl, p-tolyl, 2,5-dimethoxyphenyl, 3,4-dimethoxyphenyl, 4-ethylphenyl; and 1-phenyl-3-p-tolyl-1H-pryazole; and $R_2$ in compound A is selected from the groups consisting of: 4-bromo, 4-chloro, 4-nitro, 4-methyl, 4-methoxy, H, 3,4-dimethyl. In some embodiments the compound that is contacted with the cancer cell is compound A or a metabolite thereof. And in some embodiments the compound that is contacted with the cancer cell is the compound TDLR-505, TDLR-506, or metabolite thereof. In some embodiments the contacting step between said compound or a metabolite thereof and cancer cell occurs in vivo. And in still other embodiments the contacting step between said compound A or a metabolite thereof and the cancer cell occurs in vitro. In some embodiments the cancer cell is found in a solid tumor selected from the group consisting of: lung cancer, non-small cell, small cell, epithelial ovarian cancer, cervical cancer, colon cancer and breast cancer. Some embodiments of the invention further include the step of contacting the cancer cell with at least one chemotherapeutic reagent that binds to or damages DNA directly or reduces the activity of topoisomerase II. In some embodiments the chemotherapeutic reagent is selected from the group consisting of but not limited to: cisplatin and etoposide. Such compounds include, but are not limited to, Busulfan, Bendamustine, Carboplatin, Carmustine, Chlorambucil, Cisplatin, Cyclophosphamide, Dacarbazine, Daunorubicin, Decitabine, Doxorubicin, Epirubicin, Etoposide, Idarubicin, Ifosfamide, Irinotecan, Lomustine, Mechlorethamine, Melphalan, Mitomycin C, Mitoxantrone, Oxaliplatin, Temozolomide, Topotecan and the like.

DESCRIPTION

Figure 1A:
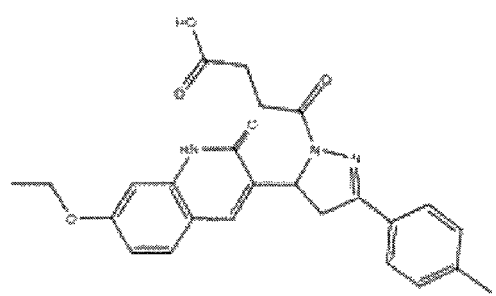
FIG. 1A. Compound 3.

For the purposes of promoting an understanding of the principles of the novel technology, reference will now be made to the preferred embodiments thereof, and specific language will be used to describe the same. It will nevertheless be understood that no limitation of the scope of the novel technology is thereby intended, such alterations, modifications, and further applications of the principles of the novel technology being contemplated as would normally occur to one skilled in the art to which the novel technology relates.

Unless specifically or implicitly stated otherwise the term 'about' as used herein means plus or minus 10 percent. For example, 'about 1.0' encompasses the range of 0.9 to 1.1.

A therapeutically effective amount is an amount of a biologically active compound that has a single or cumulative beneficial effect on the health or well being of a patient.

Inhibiting RPA-DNA interactions has the potential to impact numerous differentially regulated pathways in cancer cells. In DNA replication, RPA inhibition can be used to exploit the highly proliferative nature of cancer cells which is characterized by a large population of cells in S-phase. RPA is also essential for several DNA repair pathways in the cell including nucleotide excision repair (NER). Cisplatin, a common chemotherapeutic used in the treatment of various cancers, induces its cytotoxic effect by forming intrastrand covalent DNA adducts that are repaired primarily by the NER pathway (6). Consequently, cisplatin treatment, in conjunction with decreased RPA ssDNA binding activity, would be expected to result in decreased efficiency of cellular repair of cisplatin-DNA adducts and increased cytotoxicity. Thus, targeting RPA has the potential not only for single agent activity but also to sensitize cancer cells to therapies that induce DNA damage and genetic instability, such as cisplatin, etoposide and ionizing radiation (IR). Busulfan, Bendamustine, Carboplatin, Carmustine, Chlorambucil, Cisplatin, Cyclophosphamide, Dacarbazine, Daunorubicin, Decitabine, Doxorubicin, Epirubicin, Etoposide, Idarubicin, Ifosfamide, Irinotecan, Lomustine, Mechlorethamine, Melphalan, Mitomycin C, Mitoxantrone, Oxaliplatin, Temozolomide, Topotecan and the like.

As disclosed herein, small molecules that inhibits the ssDNA binding activity of RPA have been identified. Cellular RPA inhibition results in the inability to enter S phase, induction of cell death and synergistic activity with the chemotherapeutic reagents cisplatin and etoposide. These small molecules which are able to inhibit the ssDNA binding activity of RPA are active both as single agents and in conjunction with commonly used chemotherapeutics for killing cancer cells. In vivo, the compounds can be safely administered up to 200 mg/mg in mice IP and via oral gavage with not signs of overt toxicity and possess anticancer activity versus human non-small cell lung cancer in mouse xenograft model.

Materials and Methods

Synthesis of TDRL 505 Derivatives

Referring now to Scheme 1. Commercially available ketones such as 1 and aldehydes such as 2 care subjected to a Claisen-Schmidt condensation to create en-ones such as 3 that can be cyclized using reagents such as hydrazine to the generate H1 pyrazoles such as 4. Amide bond chemistry is used with various acids such as 5 in order to modify the N1 position of the pyrazole to form compounds such as the exemplary compound TDRL-505 6.

Scheme 1

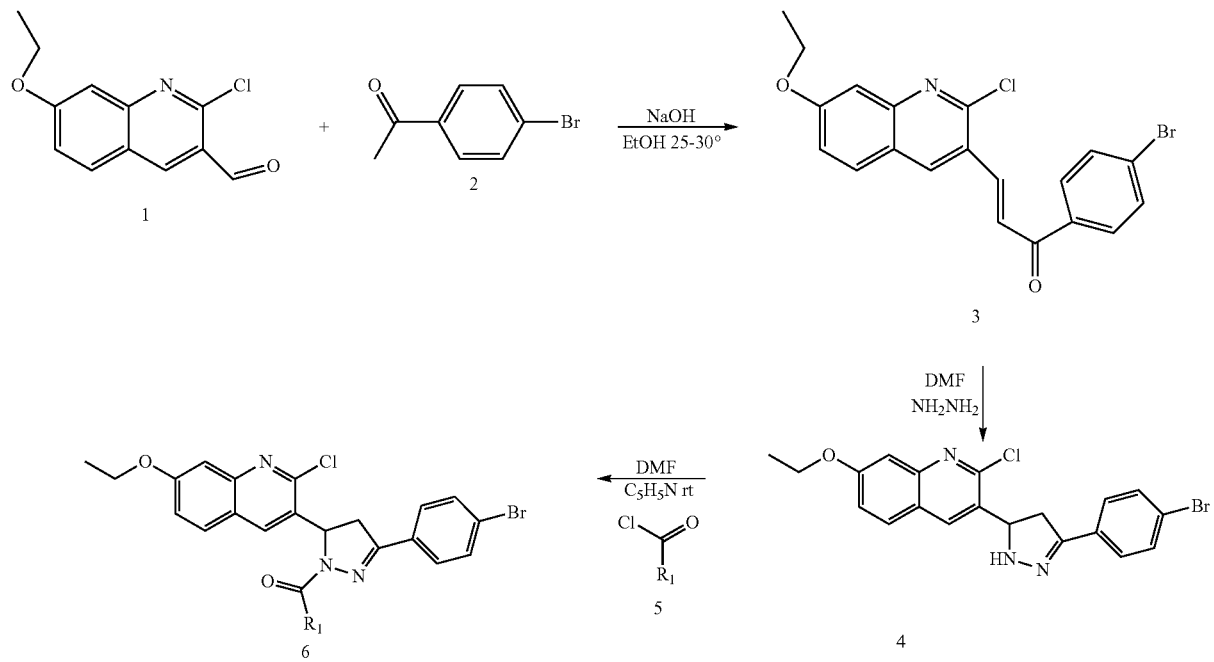

Synthesis of TDRL 506 Derivatives

Referring now to Scheme 2. TDRL-506 was prepared from TDRL-505 and 3-morpholinopropan-1-amine (2) via EDC coupling.

Scheme 2

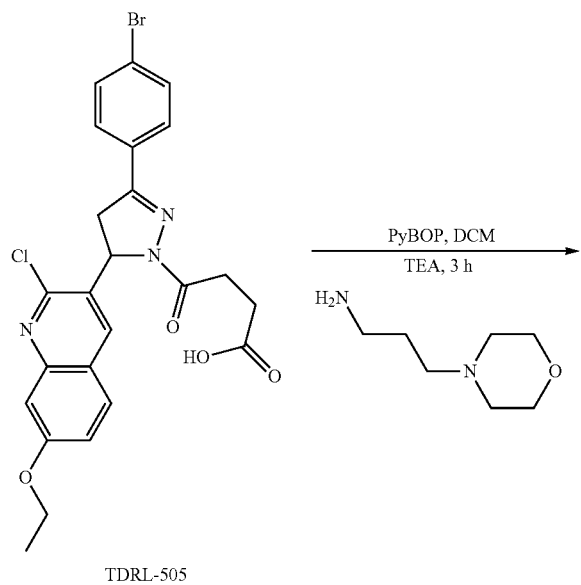

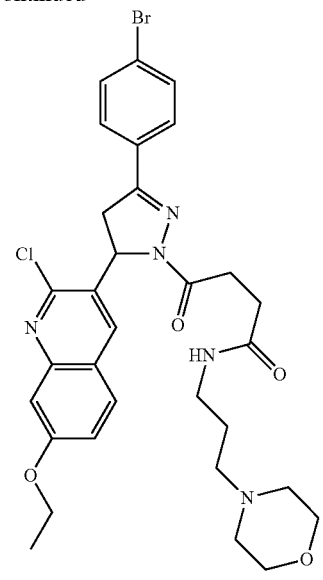

In Vitro Analysis

Small molecule inhibitors were obtained from ChemDiv and resuspended in DMSO. Compound TDLR-505 was independently synthesized and structure confirmed by mass spectrometry analysis. Human RPA was purified using an *E. coli* over expression system as previously described (7). EMSAs were performed in 20 µL reactions containing 25 nM RPA, 25 nM 5'[$^{32}$P]-labeled 34-base pair DNA as previously described (7). The final concentration of DMSO was 1%.

Flow Cytometry

H460 cells were analyzed for apoptosis using an Annexin V-FITC/Propidium iodide (PI) Vybrant Apoptosis Assay Kit (Invitrogen), according to manufacturer's instructions. Cells were plated at a density of $1 \times 10^4$ cells per $cm^2$ and allowed to adhere for 24 hours and then treated with compound TDLR-505 for 48 hours. Following plating and treatment of H460 cells as described above, adherent and non-adherent cells were collected, processed, and analyzed on a BD FACScan flow cytometer. Data was analyzed using WinMDI software (http://facs.scripps.edu/software.html). Cell cycle analysis was performed by PI staining. Briefly, cells were plated and treated with compound collected and then washed twice with PBS-EDTA supplemented with 1% BSA. Cells were fixed in 70% EtOH at $-20°$ C. while vortexing followed by incubation on ice for 30 minutes. Cells were then collected and stained with PI solution (10 µg/mL PI and 25 µg/mL RNaseA in PBS-EDTA supplemented with 1% BSA). Cells were analyzed on a Becton Dickinson FACScan flow cytometer. Cells were gated and analyzed on a histogram with events plotted against the FL2-A parameter. Cell cycle distribution was analyzed using ModFit software. G2 arrest was induced by treatment with 0.8 µg/mL nocodazole for 12 hours (10). Cells were then washed with PBS and treated with either vehicle or compound TDLR-505 (100 µM). Cells were harvested and analyzed for cell cycle distribution as described above.

Indirect Immunofluorescence

H460 cells were plated on chamber slides (LabTek) as described above. Cells were then treated for 3 hours with either 50 µM of compound TDLR-505 or vehicle as indicated and following treatment, cells were fixed in 4% paraformaldehyde at 25° C. for 3 minutes followed by washing in 0.2% Triton X-100 for 2 minutes at 4° C. The slides were then blocked in 15% FBS in PBS for 1 hour at 25° C. and then incubated with anti-RPA 34 primary antibody (Neomarkers) at a dilution of 1:500 in 15% FBS for 1 hour. Slides were then washed 3×10 minutes with 15% FBS and then incubated with Alexa Fluor-594 goat-anti-mouse secondary antibody (Invitrogen) at a dilution of 1:300 for 1 hour. Slides were again washed and stained with 300 nM DAPI diluted in PBS-EDTA for five minutes. Slides were then mounted and images captured using a Zeiss fluorescent microscope and images were captured using filters for Texas Red to visualize RPA staining and DAPI for visualizing DNA. Slides were visualized and images analyzed and quantified using ImageJ software.

Western Blot Analysis

H460 cells were plated and treated with either vehicle or 100 µM compound TDLR-505 in the presence or absence of 25 µM etoposide for 6 hours and then processed for western blot analysis using a RIPA lysis and extraction procedure. RPA was detected with an anti-RPA p34 antibody (Neomarkers) and goat anti-mouse-HRP secondary (Santa Cruz). Bands were visualized using chemiluminescence detection.

In Vivo Analysis

NOD/SCID mice (8 weeks of age) were administered IP injections of compound TDLR-505 2× per week for 2 weeks at 200 mg/kg. Mice were monitored for signs of overt toxicity and bodyweights measured three times per week. Mice were sacrificed and gross necroscopy performed to assess organ weights and inspected for signs of toxicity. There was no indication that the TDLR-505 was toxic when it was orally administered to mice at dosing level of about 200 mg/mg. NOD/SCID mice were then implanted with $5 \times 10^6$ H460 cells in 0.2 ml of 50% Matrigel subcutaneously. Tumors were allowed to develop for 7 days and TDLR-505 was administered via oral gavage 2× per week for one week. Tumor volumes were calculated by measuring the width and the length of the tumors and using these measurements in the equation: $vol.=1 \times w^2/2$.

Pharmacokinetic analysis. TDRL-505 was administered to mice at 200 mg/kg either ip or po and blood drawn at 1, 2, 4, 8, 24 and 48 hours post treatment. Serum concentration of TDRL-505 was measured using a HPLC MS/MS protocol and PK parameters analysis using on-compartmental analysis.

Results

Identification of a Small Molecule Inhibitor of RPA

Figure 1B:
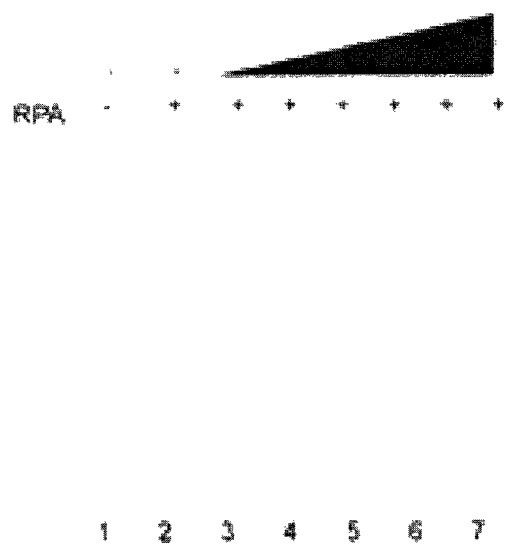
FIG. 1B. EMSA of compound 3 inhibition of RPA binding to DNA.
Figure 1C:
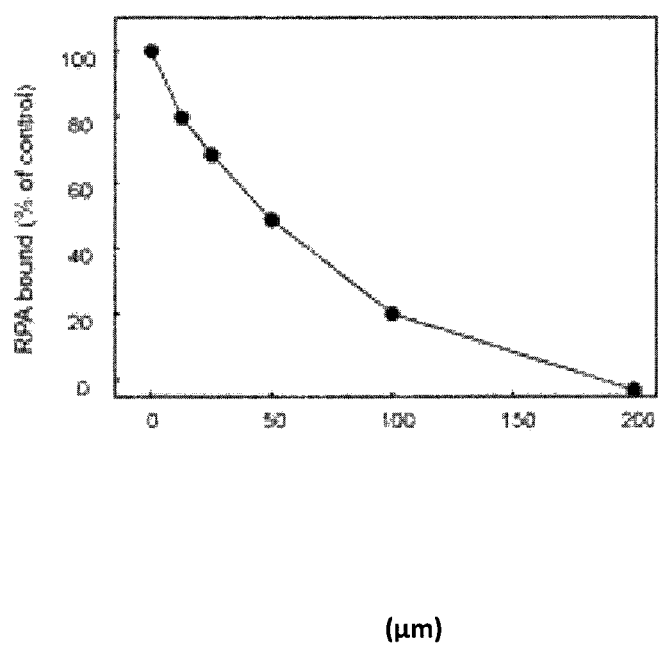
FIG. 1C. Plot of EMSA data of compound 3 inhibition of RPA binding to DNA.

Previous work led to the identification of a series of small molecules from the NCI library that inhibited the DNA binding activity of RPA but showed no cellular activity (8). A further study undertook screening of a ChemDiv library using a fluorescence polarization (FP) modification to the original assay (11). Referring now to FIGS. 1A, B, and C, compound 3 was identified from the high-throughput screen and analyzed in a secondary assay using electrophoretic mobility shift assays (EMSAs) to confirm inhibition. As illustrated by FIGS. 1B and 1C, significant inhibition of RPA DNA binding was observed via EMSA analysis and quantification of the data bears out this inhibition.

Figure 2A:
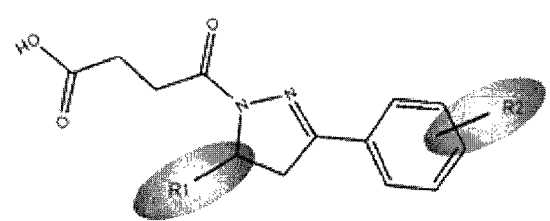
FIG. 2A. A ketobutyric acid derivative of compound A.
Figure 2B:
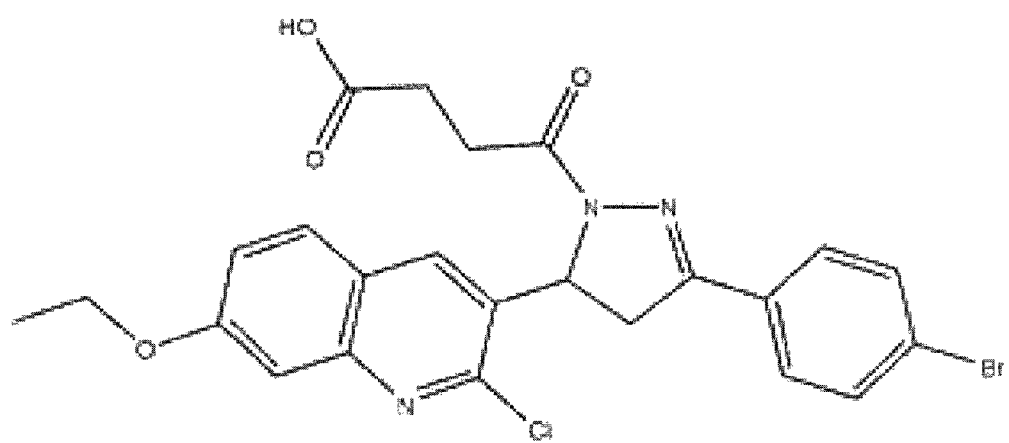
FIG. 2B. Compound TDLR-505.

Referring now to FIGS. 2A and B. In view of the high level of in vitro inhibition of RPA observed using compounds in the core structure of compound A, the core structure was substituted with dihydropyrazole with a 4-oxobutanoic acid at the N1 position and a phenyl substituent at the C3 to initiate analysis of structure activity relationships (SAR) and search for other compounds with cellular activity. Eighty-one analogs were identified and obtained from the ChemDiv library with differing substitutions off the phenyl ring ($R_2$) and varying substituents at position C5 on the dihydropyrazole ring ($R_1$) (data not shown). Among the compounds analyzed, compound TDRL-505 (FIG. 2B) was the most potent RPA inhibitor tested having an $IC_{50}$ value of 13 µM (TABLE1). A number of compounds, including TDRL 518 and TDRL 520-523 were also identified in the secondary screen as having in vitro RPA inhibitory activity, or as having chemical properties similar to the small molecules that were found to inhibit RPA activity. Still referring to TABLE 1, each compound in Table 1 was titrated against RPA in vivo or in cell, in vitro to determine its $IC_{50}$ values. As illustrated in Table 1, these compounds showed varying capacities for inhibiting RPA-ssDNA interactions (TABLE 1). In order to determine cellular activity of each of the compounds, the induction of cell death was measured in a H460 NSCLC cell line and $IC_{50}$ values for each compound following a 48 hour exposure were determined. These data are also presented in TABLE 1 and reveal a correlation between in vitro and cellular activity, consistent with cellular inhibition of RPA and indicating specificity for RPA inhibition. However, compound 523, which showed minimal inhibition of RPA-ssDNA interactions in vitro, also displayed modest cellular activity. This may be the result of the cell metabolizing the compound to generate a more effective RPA inhibitor. Analysis of the cellular and in vitro inhibitory activity of the compound 3 analogs, showed that compound TDLR-505 displayed the lowest in vitro $IC_{50}$ value and was the most potent compound of those examined in cells. Accordingly, the compound was selected for further investigation, including studying its mechanism of action and the cellular effects that result from inhibition of RPA-ssDNA interactions using a comprehensive series of in vitro, cell based and in vivo assays.

Referring now to TABLE 1, the in vitro $IC_{50}$ was determined by EMSA analysis as described in FIG. 1A. The cellular IC$_{50}$ value was determined by treating H460 cells with the indicated compounds and analyzing annexinV/PI staining as described in Methods. The in vitro and cellular data was analyzed using standard 4 parameter logistic-curve. The IC$_{50}$ values and standard error of the fit were determined from this analysis.

Referring now to Table 2. The compounds in table 2 are commercially available and have also been demonstrated to inhibit RPA-DNA binding activity in vitro. Briefly, "m" has oxo-pentanoic acid modification and a dioxinol substitution off the quinoline; "n" has oxo-pentanoic acid modification and and quinoxalin-yl-replacing the quinoline; "r" has a butanoic acid and a dioxolo substitution off the quinoline.

Derivatives of compounds m and n, which include a butyric acid and the morpholiono derivatives are made. The p-methyl is replaced with a p-bromo on the phenyl ring. Derivatives of 'r' with the Br-phenyl group and the morpholino group are also made. The SAR data described herein shows that making the butyric longer (e.g., pentanoic) appears to be somewhat detrimental to activity, but removal of the entire sidechain results in a substantial loss of RPA inhibitory activity. Accordingly, shorter derivatives of the morpholino with fewer carbons spacers are desirable.

In Vitro Inhibition of RPA's DNA Binding Activity Targeting DBD-A and B in the 70 kDa Subunit of RPA.

Figure 2C:
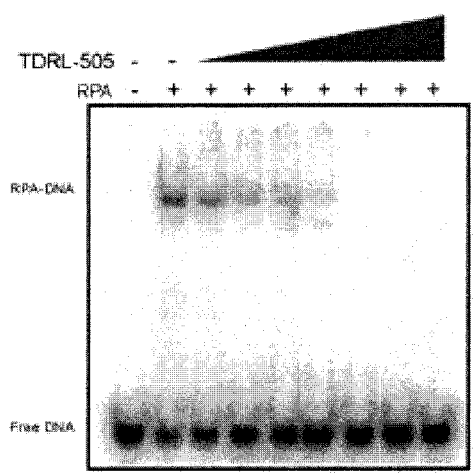
FIG. 2C. EMSA of compound TDLR-505 inhibition of RPA binding to DNA.
Figure 2D:
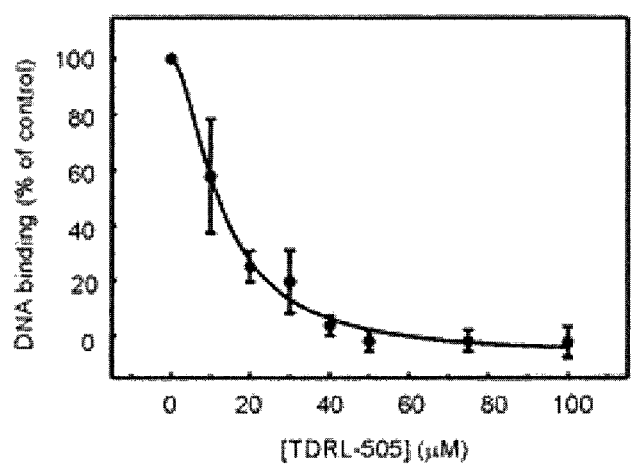
FIG. 2D. Plot of EMSA data of TDRL-505 inhibition of RPA binding to DNA.

Referring now to FIGS. 2C, D and E, EMSA analysis of compound TDLR-505, briefly, increasing concentrations of compound TDRL-505 were pre-incubated with RPA and DNA binding activity was assessed via EMSA using a 34-base ssDNA substrate. Referring now to FIG. 2D, quantification of the gel presented in FIG. 2C. Referring now to FIG. 2D, the average and standard deviation of each point are presented. The data was fit to a standard 4 parameter logistic curve with an N=4.

TABLE 1

Structure activity relationships of small molecule RPA inhibitors

| Name | Structure | IC$_{50}$ (μM) In vitro | Cellular |
|---|---|---|---|
| TDRL-505 | 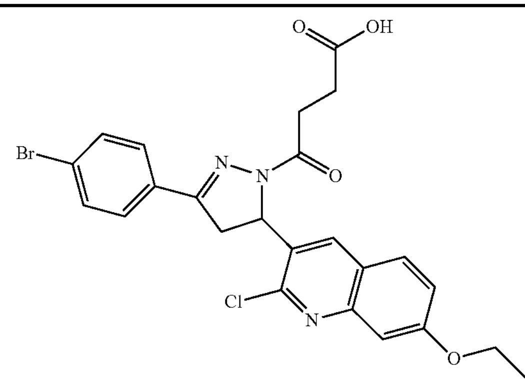 | 12.9 ± 1.3 | 30.8 ± 1.7 |
| TDRL-518 | 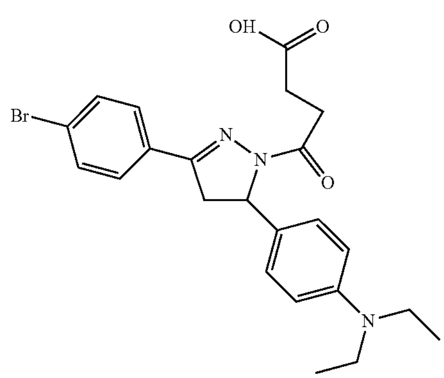 [SMILES: CCN(CC)c1ccc(C2CC(c3ccc(Br)cc3)=NN2C(=O)CCC(=O)O)cc1] | >100* | NA |
| TDRL-520 | 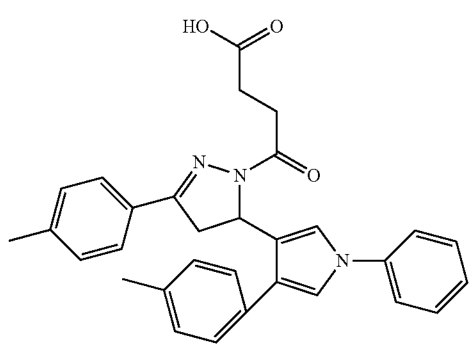 [SMILES: Cc1ccc(C2=NN(C(=O)CCC(=O)O)C(c3cn(-c4ccccc4)cc3-c3ccc(C)cc3)C2)cc1] | 20.3 ± 10.7 | 49.9 ± 2.5 |

TABLE 1-continued
Structure activity relationships of small molecule RPA inhibitors
| Name | Structure | IC$_{50}$ ($\mu$M) | |
|---|---|---|---|
| | | In vitro | Cellular |
| TDRL-521 | 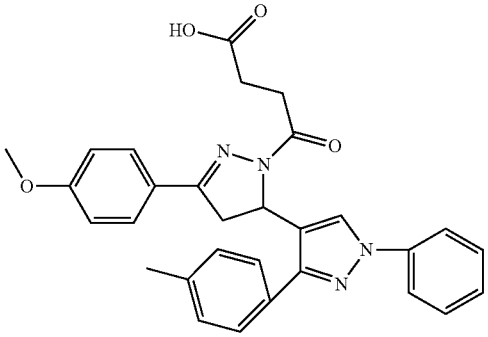 [SMILES: COc1ccc(C2=NN(C(=O)CCC(=O)O)C(c3cn(-c4ccccc4)nc3-c3ccc(C)cc3)C2)cc1] | 71.7 ± 33.9 | 56.9 ± 6.7 |
| TDRL-522 | 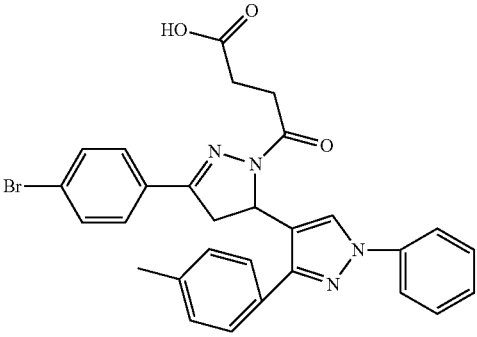 [SMILES: Cc1ccc(-c2nn(-c3ccccc3)cc2C2CC(c3ccc(Br)cc3)=NN2C(=O)CCC(=O)O)cc1] | 56.1 ± 6.7 | 38 ± 32*** |
| TDRL-523 | 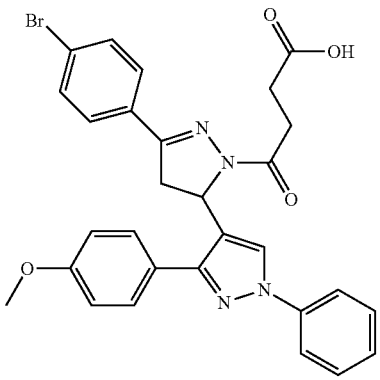 [SMILES: COc1ccc(-c2nn(-c3ccccc3)cc2C2CC(c3ccc(Br)cc3)=NN2C(=O)CCC(=O)O)cc1] | >100** | 31.0 ± 5.2 |
*inhibition at the highest concentration tested (100 μM) was 9%;
**inhibition at the highest concentration tested (100 μM) was 36%;
***Maximum observed cytotoxicity was 80% of control

TABLE 2

| Structure | Properties |
|---|---|
| "m" (structure shown) | 5-(5-(7-chloro-2,3-dihydro-[1,4]dioxino[2,3-g]quinolin-8-yl)-3-(p-tolyl)-4,5-dihydro-1Hpyrazol-1-yl)-5-oxopentanoic acid<br>Chemical Formula: $C_{26}H_{24}ClN_3O_5$<br>Exact Mass: 493.14<br>Molecular Weight: 493.94<br>m/z: 493.14 (100.0%), 495.14 (33.3%), 494.14 (29.4%), 496.14 (9.2%), 495.15 (3.9%), 497.14 (1.6%)<br>Elemental Analysis: C, 63.22; H, 4.90; Cl, 7.18; N, 8.51; O, 16.20 |
| "n" (structure shown) | 5-oxo-5-(3-phenyl-5-(quinoxalin-6-yl)-4,5-dihydro-1H-pyrazol-1-yl)pentanoic acid<br>Chemical Formula: $C_{22}H_{20}N_4O_3$<br>Exact Mass: 388.15<br>Molecular Weight: 388.43<br>m/z: 388.15 (100.0%), 389.16 (24.1%), 390.16 (3.4%), 389.15 (1.5%)<br>Elemental Analysis: C, 68.03; H, 5.19; N, 14.42; O, 12.36 |
| "r" (structure shown) | 4-(5-(6-chloro-[1,3]dioxolo[4,5-g]quinolin-7-yl)-3-(p-tolyl)-4,5-dihydro-1H-pyrazol-1-yl)-4-oxobutanoic acid<br>Chemical Formula: $C_{24}H_{20}ClN_3O_5$<br>Exact Mass: 465.11<br>Molecular Weight: 465.89<br>m/z: 465.11 (100.0%), 467.11 (33.3%), 466.11 (27.3%), 468.11 (8.5%), 467.12 (3.3%), 469.11 (1.5%)<br>Elemental Analysis: C, 61.87; H, 4.33; Cl, 7.61; N, 9.02; O, 17.17 |

Modification of TDRL-505; Analysis of TDRL-506

Figure 3:
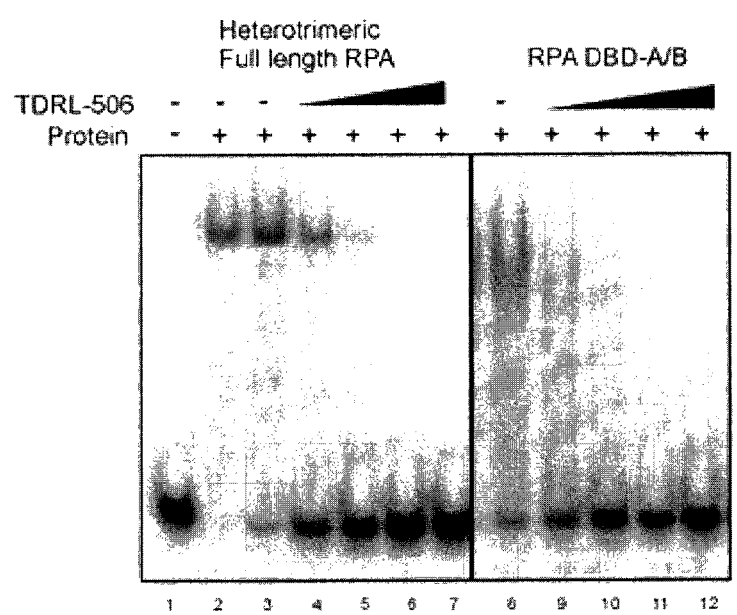
FIG. 3. EMSA of compound TDLR-506 inhibition of RPA binding to DNA.

Referring now to Scheme 2. TDRL-506 was synthesized and purified and assessed for in vitro RPA inhibitory activity. Referring to FIG. 3, TDRL-506 was assessed for RPA inhibitory activity against both full length RPA heterotrimer Lanes 1-7 and the DBD-A/B construct (lanes 8-12). The concentrations used were 25, 50, 75 and 100 □M TDRL-506. The data demonstrate that the TDRL-506 compound containing the morpholino modification retains full RPA inhibitory activity.

Induction Cancer Cell Death by TDRL-505.

Figure 4A:
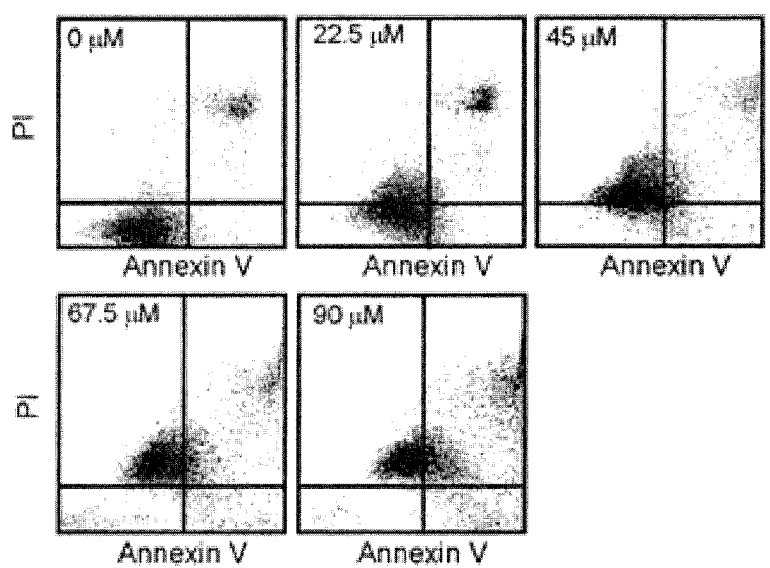
FIG. 4A. Dot plots of H460 cells stained with Annexin V/PI measuring cell death induced by TDRL-505.
Figure 4B:
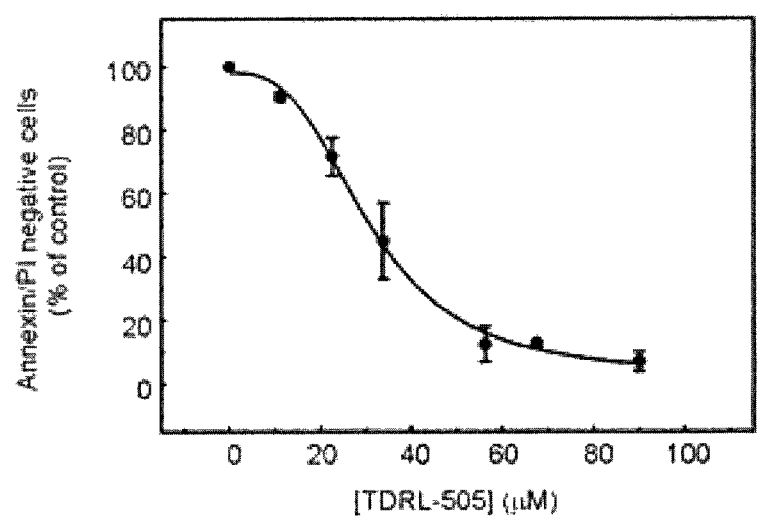
FIG. 4B. Plot of cell death data measured at different concentrations of compound TDLR-505.

Referring now to FIGS. 4A, 4B, 4C and 4D, the effects of compound TDRL-505 on induction of cell death and cell cycle progression in a H460 NSCLC cell line was measured. Briefly, H460 cells were treated with compound TDRL-505 for 48 hours and analyzed for cell viability via staining with AnnexinV/PI and presented as dot plots (see FIG. 3A). Referring now to FIG. 4B, the data from FIG. 4A was quantified and the percentage of Annexin-/PI-cells (lower left quadrant), indicating live cells, was calculated. The average±SD (N=4) are presented and the data was fit to a 4-parameter logistic curve. These data demonstrate that TDRL-505 is capable of inducing cell death in NSCLC cells. As an independent measure of the effect of compound TDLR-505 on cell viability, a crystal violet staining assay was used and gave an $IC_{50}$ value of 64 μM (data not shown). A similar result was also observed in treatment of the A549 NSCLC cell line with compound TDLR-505 while analysis using freshly isolated peripheral blood mononuclear cells (PBMCs) revealed minimal cytotoxic activity (data not shown). In these experiments, compound TDLR-505 shows significant cytotoxic effects in NSCLC cell lines and only modest activity in non-cancerous cells, indicating that there is a therapeutic treatment window for these molecules.

Figure 4C:
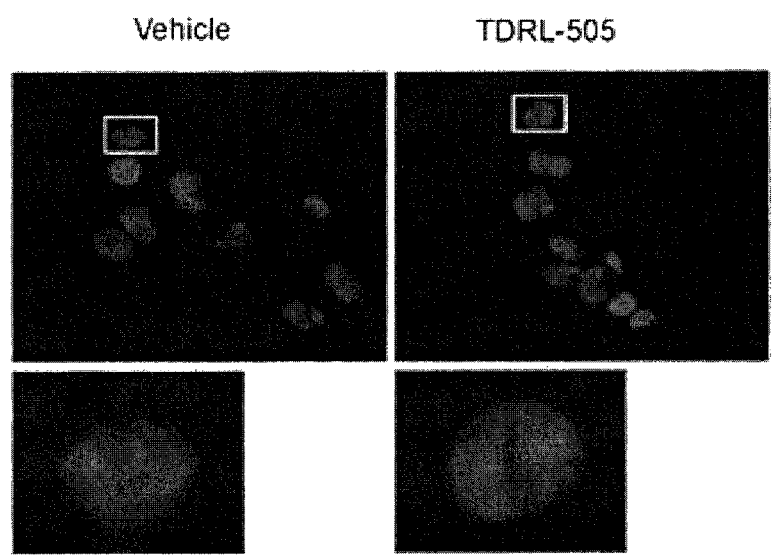
FIG. 4C. Immuno-fluorescence of RPA cellular localization probed with an anti-RPA antibody and visualized with an AlexaFlour antibody.
Figure 4D:
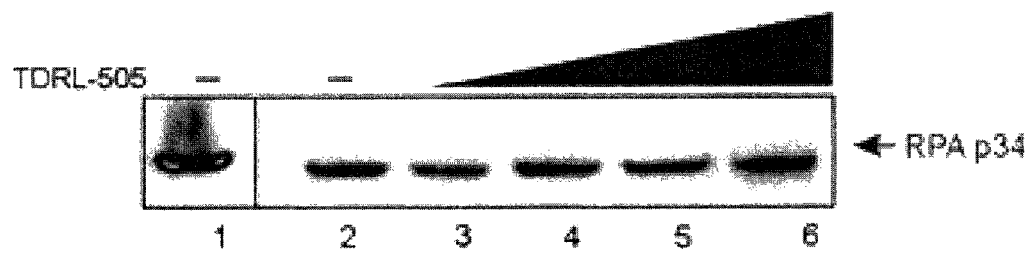
FIG. 4D. Western blots of the of the p34 subunit of RPA as a function of treatment with compound TDRL-505.

These cellular effects seen following treatment with compound TDLR-505 correlate with an inability of RPA to interact with DNA which could then result in numerous possibilities including degradation or redistribution of RPA within the cell. Indirect immunofluorescence was used to assess how inhibition of RPA binding influences cellular localization. Referring now to FIG. 4C, H460 cells were treated with 50 µM compound TDLR-505 or vehicle for 3 hours and analyzed for RPA expression and localization by indirect immunofluorescence using an Alexa Fluor594 secondary antibody (red). Slides were counter stained with DAPI (blue) and images merged. Magnification of the boxed cells is presented below the low magnification images. Briefly, after 3 hours of treatment with compound TDLR-505, cells showed a decrease in the intensity of RPA staining compared to vehicle treated control without a change in overall sub-cellular localization. (FIG. 4C). Quantification of the intensity of staining revealed that of cells treated with vehicle, 23% showed intensity >70% of the maximum, while cells treated with compound showed only 15% above that value. These data demonstrate that treatment of cells with TDRL-505 reduces the amount of RPA bound to DNA in cells. Referring now to FIG. 4D, H460 cells were treated with vehicle or 100 µM compound TDLR-505 without or with etoposide (25 µM) as indicated in the figure. RPA expression was assessed via western blot analysis probing for the p34 subunit. Lane 1 is a positive control with RPA purified from an E. coli expression system. The position of un-phosphorylated RPA p34 and hyper-phosphorylated RPA p34 are indicated by the arrows. These data demonstrate that RPA is not degraded or reduced in expression as a function of TDRL-505 treatment.

Compound TDLR-505 Induces a G1 Arrest in H460 Cell Lines.

The compound TDLR-505 was tested to assess its affect on cell cycle progression. Knockdown of RPA by siRNA has been demonstrated to induce a G1 cell cycle arrest consistent with the essential role of RPA in the initiation of S-phase DNA replication (19). In order to determine if this is the same mechanism of action displayed by compound TDLR-505, its affect on H460 cell cycle progression was measured. As illustrated by the data presented in FIG. 5, synchronized H460 cells show an inability to re-enter S-phase when treated with TDRL-505.

Figure 5A:
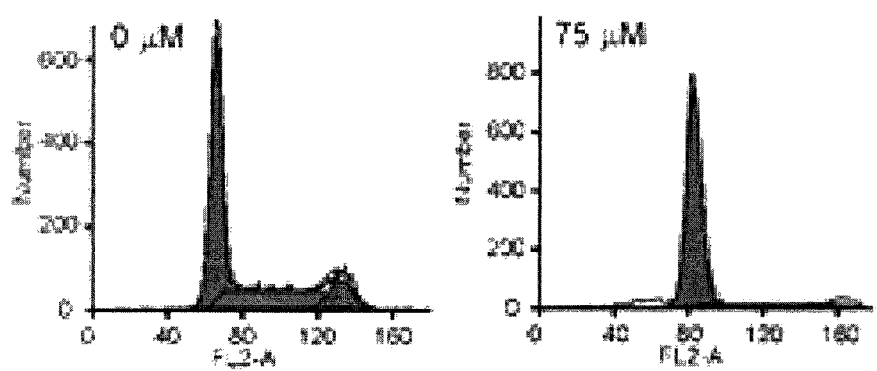
FIG. 5A. Cell cycle distribution of H460 NSCLC cells treated with compound TDLR-505.
Figure 5B:
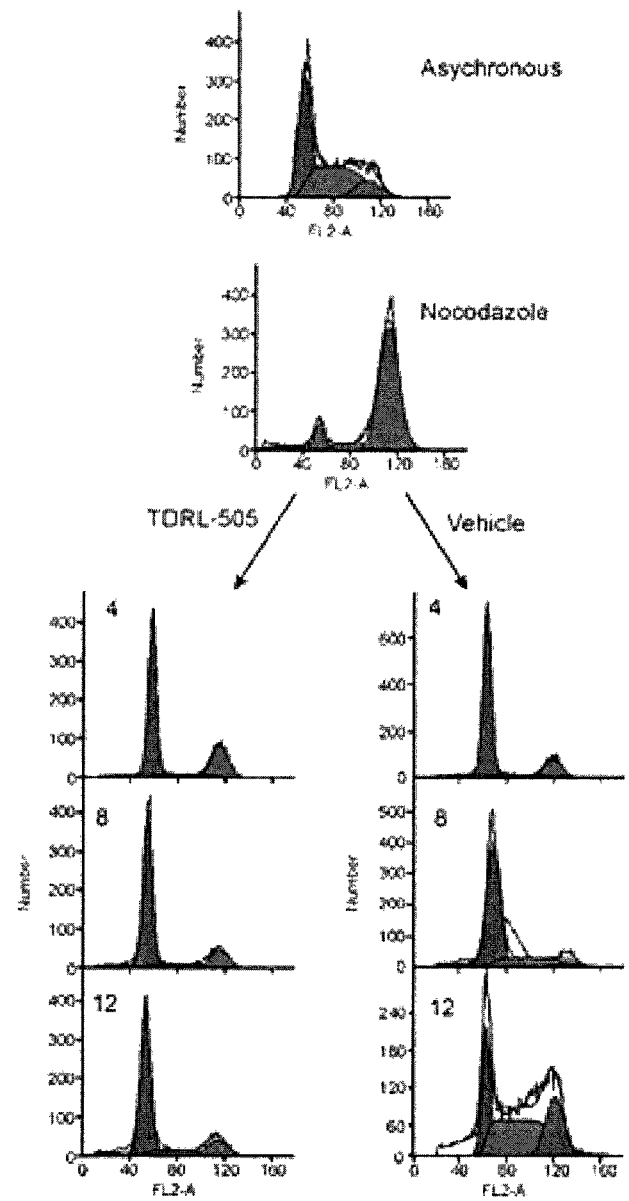
FIG. 5B. Cell cycle distribution of H460 cells treated with Nocodazole and then compound TDLR-505 for 4, 8 or 12 hours.

Referring now to FIG. 5A. H460 NSCLC cells were treated with 0 and 75 µM of compound TDLR-505 for 48 hours and then analyzed for cell cycle distribution using flow cytometry. FIG. 5B, H460 cells were treated with 0.8 µg/mL nocodazole for 12 hours, washed then treated with either vehicle or 100 µMTDLR-505 for 4, 8 and 12 hours. Cells were then harvested and analyzed for cell cycle distribution using flow cytometry.

The analysis of compound TDRL-505 on an asynchronous culture was tested and an increase in the proportion of cells in G1-phase was observed in response to treatment with TDRL-505 (FIG. 5A). To determine if entry into S-phase is inhibited in compound TDLR-505 treated cells, cells were synchronized in G2/M with nocodazole and then released from G2 arrest and re-fed complete medium supplemented with either vehicle or compound TDLR-505. Referring now to FIG. 5B, both control and treated cells rapidly progressed through mitosis into G1 after removal of nocodazole. Cells that were treated with vehicle alone entered into G1, as seen at the 4 hour time point and progression into S-phase is apparent at the 8 hour time point with progression into G2 evident at the 12 hour time point. Cells that were treated with compound TDLR-505 after release from nocodazole progressed into G1 phase of the cell cycle but did not enter S-phase even 12 hours post release. These data demonstrate that TDRL-505 induced a G1 cell cycle arrest in lung cancer cells.

Inhibition of RPA's Role in DNA Repair and Replication.

Figure 6:
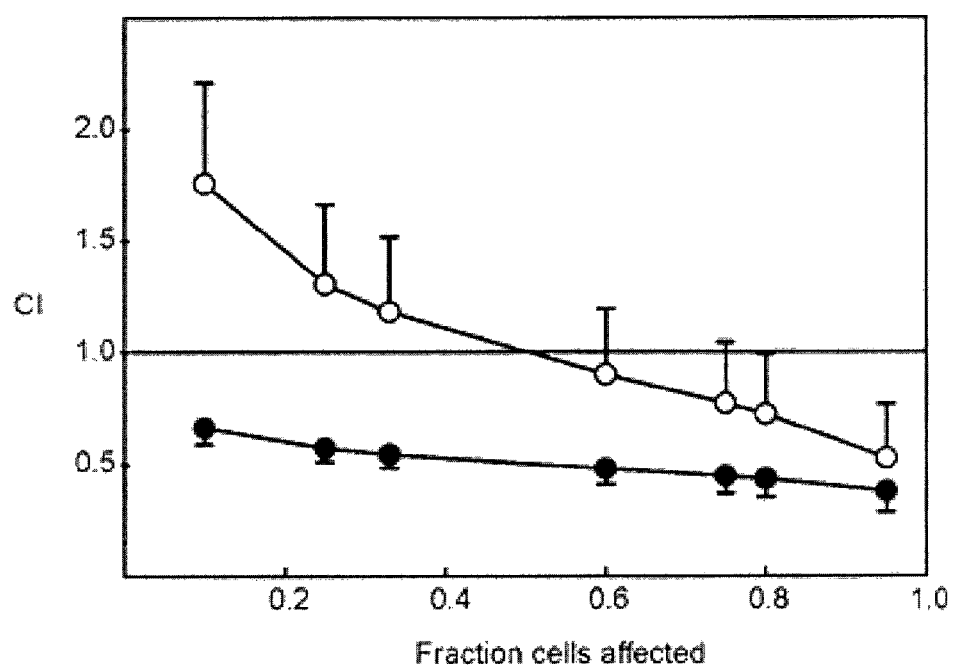
FIG. 6. Analysis of synergy in H460 cells co-treated with compound TDLR-505 and either cisplatin (open circles) or etoposide (closed circles).

In addition to its essential role in DNA replication, RPA is required for the repair of bulky DNA adducts as well as DNA breaks induced by various types of exogenous and endogenous agents. The association of RPA with ssDNA is a critical feature of all of these pathways, indicating that inhibition of this activity would increase the cytotoxic effects induced by DNA damage. In order to determine the effect of RPA inhibition on cellular sensitivity to cisplatin, the combination index (CI) (20) was measured. Referring now to FIG. 6. As illustrated in this experiment, compound TDLR-505 acts synergistically with both cisplatin and etoposide in H460 cells. H460 cells were treated with increasing fractions of the $IC_{50}$ concentration of either cisplatin or etoposide with compound TDLR-505 for 48 hours. After treatment, cells were harvested and analyzed by annexin V/PI flow cytometry. Open circles indicate CI analysis of cisplatin with TDLR-505 and closed circles represent etoposide with TDLR-505. The combination index analysis was performed as previously described (20). The data are presented as the average±SD from (N=3). When cisplatin and compound TDLR-505 were used in combination, cell viability was decreased to a level that was greater than that induced by either agent alone, resulting in a synergy between the two compounds and CI of 0.4 at the highest fraction of cells affected. The interaction became additive and then antagonistic (revealed from CI values greater than one) at lower fractions of cells affected. These results demonstrate that compound TDLR-505 is able to potentiate the effect of cisplatin in H460 cells and is consistent with inhibition of the cellular activity of RPA in NER. The ability of compound TDLR-505 to synergize with etoposide was also examined. Etoposide induces replication fork arrest and DNA damage response, both cellular processes that require RPA (21). Using the same analysis as described above for cisplatin, compound TDLR-505 showed synergistic activity with etoposide at all fractions of cells affected (FIG. 6). RPA p34 has been shown to be hyper-phosphorylated in response to etoposide treatment in a variety of cellular systems (21; 22). Interestingly, analysis of RPA p34 hyperphosphorylation by western blot analysis was not altered by concurrent treatment with TDLR-505 and no dramatic change in overall RPA expression was evident (FIG. 4D). This data demonstrate that treatment with TDLR-505 does not dramatically impact etoposide dependent DNA damage signaling response and that synergy is observed in the presence of RPA hyperphosphorylation.

In Vivo Analysis of Compounds TDLR-505.

Referring now to Table 3. TDRL-505 demonstrating reasonable $IC_{50}$ values against NSCLC prompted the assessment in vivo of the effect of RPA inhibition on lung cancer tumor growth. The safety of administration of TDRL-505 in naive mice was determined Additional data demonstrated that IP administration of compound TDLR-505 in a formulation of 25% DMSO in 0.75% Tween 80 to NOD/SCID mice is well tolerated up to 400 mg/kg. Oral dosing in 0.1% Tween 80/methylcellulose was also well tolerated up to 800 mg/kg.

Figure 7A:
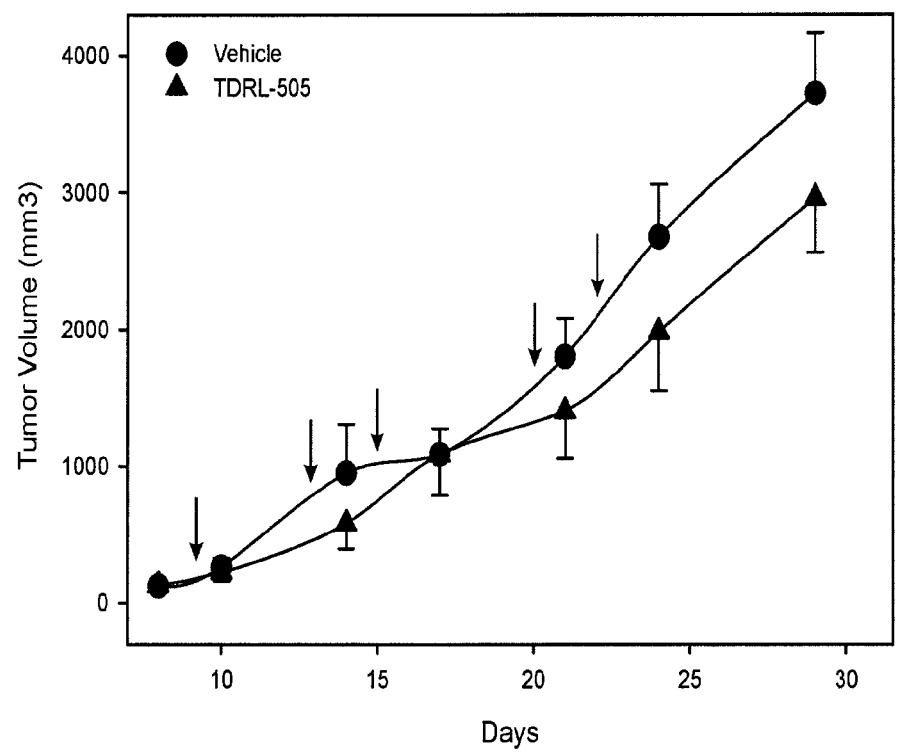
FIG. 7A. In vivo anticancer activity of TDRL-505 versus non-small cell lung cancer in a mouse xenograft model. Tumor volume was measured and plotted versus time. Data are presented as the mean±S.E (n=5).
Figure 7B:
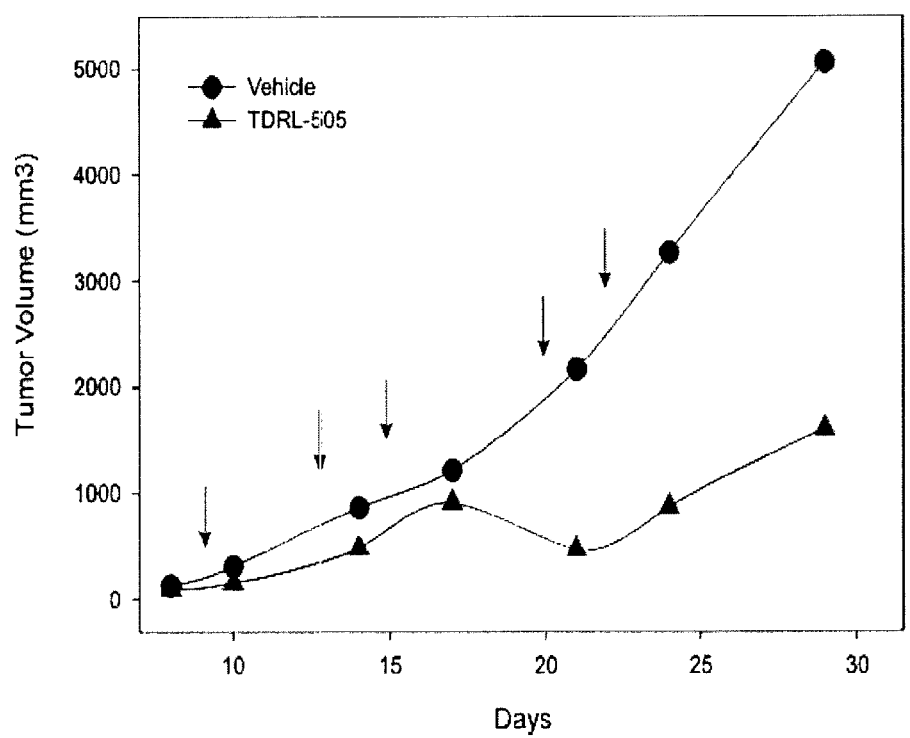
FIG. 7B. In vivo anticancer activity of TDRL-505 versus non-small cell lung cancer in an individual mouse assessed in the xenograft model.

Mice that had been implanted with a human NSCLC tumor cells were subjected to a regime of oral dosing. The tumors were allowed to grow to 100 mm3 after which treatment with TDRL-505 or vehicle was commenced. The results presented in (FIG. 7) demonstrate a reduction in tumor growth in mice treated with TDRL-505 compared to the vehicle control. Referring to FIG. 7B, analysis of individual mice reveal significant reduction in tumor growth compared to vehicle treated controls.

Based on the in vivo anticancer activity of TRL-505 a comparison of pharmacokinetic parameters with both ip and po dosing regimens was made. Naive mice were given a single dose and as described in Table 3, blood was drawn at various time intervals and TRDL-505 concentration determined via a HPCL/MSMS protocol developed for this compound. The data demonstrate significantly better PK parameters in nearly all parameters for ip dosing compared to po. These data suggest the ip dosing will yield significantly greater bioavailability and lead to enhanced efficacy leading to even greater anti cancer activity. In addition, the morpholino-modification employed in TDRL-506 should increase is oral bioavailability thereby rendering more effective oral dosing regimens for TDRL-506.

than the number of cells that are in S-phase. This illustrates the existence of a therapeutic window for specifically targeting actively dividing cells in the context of cancer treatment using SMIs to block the cellular activity of RPA.

The role of RPA in DNA repair also allows for inhibition of its activity to increase the efficacy of current chemotherapeutics that induce DNA damage in the context of combination therapy. The inhibition of DNA repair is anticipated to result in persistent DNA damage which would increase cytotoxicity. The indispensable role of RPA in the recognition and verification steps of NER is well characterized and, in addition, RPA participates in the re-synthesis step following excision of the damaged oligonucleotide (25). Previous studies have shown that cells with decreased levels of NER proteins demonstrate increased sensitivity to cisplatin treatment (26). Consistent with this, our data reveal a synergistic interaction between compound TDLR-505 and cisplatin at high fractions of cells affected. Interestingly, at low fractions of cells affected, an antagonistic interaction is observed with combination indices greater than one. This is likely the result

TABLE 3

TDRL-505 Pharmacokinetics: Noncompartmental analysis

| Dose (mg/Kg) | Route | Formulation | Weight (avg) (Kg) | $C_{max}$ (ng/mL) | $t_{max}$ (hours) | $AUC_{0-t}$ (ng * mL$^{-1}$ * hr) | $t_{1/2}$ (hours) | Cl/F (mL/hr) | $Vd_{ss}$ (L) |
|---|---|---|---|---|---|---|---|---|---|
| 200 | IP | Tween80/DMSO | 0.0242 | 31702 | 8 | 577143 | 7.13 | 8.29 | 0.11 |
| 200 | PO | Methylcellulose/DMSO | 0.0253 | 6397 | 1 | 24971 | 2.62 | 202.33 | 0.88 |

$C_{max}$: maximum concentration
$t_{max}$: time of maximum concentration
$AUC_{0-t}$: area under the plasma concentration-time curve up to time, t
Cl/F: clearance/availability; If dosage is IV, then F = 1.
$Vd_{ss}$: apparent volume of distribution at steady state; $Vd_{ss} = t_{1/2}$: half-life Advances in high throughput screening and chemical libraries have resulted in an explosion of putative cancer targets and their inhibitors. To date, the majority of these target enzymatic activity associated with a specific protein. As illustrated herein, targeting the non-enzymatic DNA binding activity of RPA opens up an entire new class of putative interactions. Compound TDLR-505 blocks cell entry into S-phase and results in a cytotoxic/cytostatic response, the result is consistent with inhibiting RPA's role in the initiation of DNA replication and this process likely involves a complex series of interactions, one of which is the loading of RPA at replication origins in a S-phase CDK dependent process (19; 23). While these data demonstrate no appreciable DNA synthesis, it remains to be determined if RPA is able to load at origins in cells treated with compound TDLR-505. The exit of cells from S-phase into G2 in the presence of TDLR-505 suggests that DBD-A and -B DNA interactions may be less important in elongation, in which RPA predominantly participates in lagging strand DNA synthesis (24). RPA's role in the early stages of DNA replication would predict a G1-arrest as opposed to an intra S-phase arrest, which we observed. However, the potential that S-phase cells treated with compound TDLR-505 have reduced RPA binding and hence blocked elongation and firing of late replication forks cannot be ruled out. This presents the possibility that cells killed by compound TDLR-505 are those actively replicating their DNA and the interruption of this causes the observed cytotoxicity. However, the continuation of G1 arrest may also induce cell death after prolonged periods of time, explaining why the degree of cell death after 48 hours of treatment is greater of interactions not at the level of repair but at the level of signaling. As cisplatin leads to activation of a G2 checkpoint and induces apoptosis from an extended G2 arrest, the finding that compound TDLR-505 blocks cells in G1 indicates that fewer cells would be subject to cisplatin induced G2 arrest. Likewise, if compound TDLR-505 toxicity stems from an extended G1 arrest, the G2 checkpoint induced by cisplatin would result in less cell death as a result of treatment. At high concentrations, this effect is mitigated by the interaction at the level of DNA repair with RPA inhibition increasing cisplatin toxicity and overcoming the antagonistic signaling interaction.

The role of RPA in DNA replication restart and processing of collapsed replication forks also presents opportunities for combination therapy (27; 28). Interestingly, combination index analysis of the activity of etoposide with compound TDLR-505 showed synergistic activity at all fractions of cells affected. Etoposide inhibits the enzymatic activity of topoisomerase II (topo II) resulting in persistent covalent-cleavage complexes on DNA which lead to replication fork arrest and both single and double strand breaks (29). RPA has been demonstrated to respond to and repair these types of lesions and DNA intermediates and inhibiting this activity would be expected to potentiate the effects seen by inhibiting topo II, which is observed in our analyses (21). Secondly, due to the asynchronous nature of these cells, at any given time a cell undergoing replication would be expected to be in various stages of replication firing. RPA is required in early replication firing, while topo II has been shown to be required for later stage replication events (30). Therefore, inhibition of both stages of replication progression would be expected to show a greater effect than inhibiting either one of the steps individually, which would implicate a synergistic relationship between compound TDLR-505 and etoposide. Inhibition of RPA activity and abrogation of pathway function has the potential for widespread utility in cancer treatment. The role of RPA in several other repair pathways opens up other opportunities for combination therapy using RPA inhibitor. For example, combining molecularly targeted RPA inhibition with radiation therapy could lead to increased cytotoxicity in tumor cells via inhibition of DNA double strand break repair via non-homologous DNA end joining or homologous recombination, both of which have been shown to require RPA (31-33).

While targeting the enzymatic activity of proteins with small molecules is well accepted, the results presented herein demonstrate the feasibility and utility of targeting a non-enzymatic protein-DNA interaction. These compounds are Small Molecule Inhibitor (SMIs) of RPA which display both in vitro and cellular activity. The approach of targeting RPA for cancer chemotherapy has several unique advantages including the lack of redundancy resulting from the absence of efficient back-up systems necessary to counteract the loss of RPA activity. Inhibition of RPA will have broad spectrum utility as the reliance on RPA for increased cell proliferation and repair of chemotherapeutic DNA damaging agents is not unique to any single cancer. Targeting the DNA binding activity of RPA with small, drug-like molecules as disclosed herein illustrates that this class of proteins can be targeted to produce therapeutic compounds.

While the novel technology has been illustrated and described in detail in the figures and foregoing description, the same is to be considered as illustrative and not restrictive in character, it being understood that only the preferred embodiments have been shown and described and that all changes and modifications that come within the spirit of the novel technology are desired to be protected. As well, while the novel technology was illustrated using specific examples, theoretical arguments, accounts, and illustrations, these illustrations and the accompanying discussion should by no means be interpreted as limiting the technology. All patents, patent applications, and references to texts, scientific treatises, publications, and the like referenced in this application are incorporated herein by reference in their entirety.

REFERENCES (1) Wold M S. Replication protein A: a heterotrimeric, single-stranded DNA-binding protein required for eukaryotic DNA metabolism. [Review] [190 refs]. Annual Review of Biochemistry 1997; 66:61-92.
(2) Bochkarev A, Bochkareva E. From RPA to BRCA2: lessons from single-stranded DNA binding by the OB-fold. Current Opinion in Structural Biology 2004 February; 14(1):36-42.
(3) Fanning E, Klimovich V, Nager A R. A dynamic model for replication protein A (RPA) function in DNA processing pathways. Nucleic Acids Res 2006; 34(15):4126-37.
(4) Bochkarev A, Pfuetzner R A, Edwards A M, Frappier L. Structure of the single-stranded-DNA-binding domain of replication protein A bound to DNA. Nature 1997; 385 (6612):176-81.
(5) Pfuetzner R A, Bochkarev A, Frappier L, Edwards A M. Replication protein A. Characterization and crystallization of the DNA binding domain. J Biol Chem 1997; 272(1):430-4.
(6) Zamble D B, Mu D, Reardon J T, Sancar A, Lippard S J. Repair of cisplatin—DNA adducts by the mammalian excision nuclease. Biochemistry 1996; 35(31):10004-13.
(7) Patrick S M, Turchi J J. Replication Protein A (RPA) Binding to Duplex Cisplatin-damaged DNA Is Mediated through the Generation of Single-stranded DNA. J Biol Chem 1999; 274(21):14972-8.
(8) Andrews B J, Turchi J J. Development of a high-throughput screen for inhibitors of replication protein A and its role in nucleotide excision repair. Mol Cancer Ther 2004; 3(4):385-91.
(9) Goodsell D S, Morris G M, Olson A J. Automated docking of flexible ligands: applications of AutoDock. J Mol Recognit 1996 January; 9(1):1-5.
(10) Jin Z, Dicker D T, el-Deiry W S. Enhanced sensitivity of G1 arrested human cancer cells suggests a novel therapeutic strategy using a combination of simvastatin and TRAIL. Cell Cycle 2002 January; 1(1):82-9.
(11) Turchi J J, Shuck S C, Short E A, Andrews B J. Targeting Nucleotide Excision Repair as a Mechanism to Increase Cisplatain Efficacy. In: Bonetti A, Leone R, Muggia F M, Howell S B, editors. Platinum and Other Heavy Metal Compounds in Cancer Chemotherapy. New York: Humana Press; 2009. p. 177-88.
(12) Dodson G E, Shi Y, Tibbetts R S. DNA replication defects, spontaneous DNA damage, and ATM-dependent checkpoint activation in replication protein A-deficient cells. J Biol Chem 2004 Aug. 6; 279(32):34010-4.
(13) Patrick S M, Oakley G G, Dixon K, Turchi J J. DNA Damage Induced Hyperphosphorylation of Replication Protein A. 2. Characterization of DNA Binding Activity, Protein Interactions, and Activity in DNA Replication and Repair. Biochemistry 2005 Jun. 14; 44(23):8438-48.
(14) Patrick S M, Turchi J J. Xeroderma pigmentosum complementation group A protein (XPA) modulates RPA-DNA interactions via enhanced complex stability and inhibition of strand separation activity. J Biol Chem 2002; 277(18):16096-101.
(15) Patrick S M, Turchi J J. Stopped-flow kinetic analysis of replication protein A-binding DNA—Damage recognition and affinity for single-stranded DNA reveal differential contributions of k(on) and k(off) rate constants. J Biol Chem 2001; 276(25):22630-7.
(16) Bochkareva E, Belegu V, Korolev S, Bochkarev A. Structure of the major single-stranded DNA-binding domain of replication protein A suggests a dynamic mechanism for DNA binding. EMBO J 2001; 20(3):612-8.
(17) Dispersyn G, Nuydens R, Connors R, Borgers M, Geerts H. Bcl-2 protects against FCCP-induced apoptosis and mitochondrial membrane potential depolarization in PC12 cells. Biochim Biophys Acta 1999 Aug. 5; 1428(2-3):357-71.
(18) Palermo C M, Bennett C A, Winters A C, Hemenway C S. The AF4-mimetic peptide, PFWT, induces necrotic cell death in MV4-11 leukemia cells. Leuk Res 2008 April; 32(4):633-42.
(19) Haring S J, Mason A C, Binz S K, Wold M S. Cellular functions of human RPA1. Multiple roles of domains in replication, repair, and checkpoints. J Biol Chem 2008 Jul. 4; 283(27):19095-111.
(20) Chou T C, Talalay P., Quantitative-analysis of dose-effect relationships—the combined effects of multiple-drugs or enzyme-inhibitors. Advances in Enzyme Regulation 1984; 22:27-55.

(21) Robison J G, Bissler J J, Dixon K. Replication protein A is required for etoposide-induced assembly of MRE11/RAD50/NBS1 complex repair foci. Cell Cycle 2007 Oct. 1; 6(19):2408-16.

(22) Block W D, Yu Y, Lees-Miller S P. Phosphatidyl inositol 3-kinase-like serine/threonine protein kinases (PIKKs) are required for DNA damage-induced phosphorylation of the 32 kDa subunit of replication protein A at threonine 21. Nucleic Acids Res 2004; 32(3):997-1005.

(23) Tanaka T U, Nasmyth K. Association of RPA with chromosomal replication origins requires an Mcm protein, and is regulated by Rad53, and cyclin- and Dbf4-dependent kinases. EMBO J 1998 Sep. 1; 17(17):5182-91.

(24) Hubscher U, Seo Y S. Replication of the lagging strand: a concert of at least 23 polypeptides. Mol Cells 2001 Oct. 31; 12(2):149-57.

(25) Hess M T, Schwitter U, Petretta M, Giese B, Naegeli H. Bipartite substrate discrimination by human nucleotide excision repair. Proc Natl Acad Sci USA 1997; 94(13): 6664-9.

(26) Welsh C, Day R, McGurk C, Masters J R W, Wood R D, Koberle B. Reduced levels of XPA, ERCC1 and XPF DNA repair proteins in testis tumor cell lines. Int J Cancer 2004; 110(3):352-61.

(27) Wang L C, Stone S, Hoatlin M E, Gautier J. Fanconi anemia proteins stabilize replication forks. DNA Repair (Amst) 2008 Dec. 1; 7(12):1973-81.

(28) Manthey K C, Opiyo S, Glanzer J G, Dimitrova D, Elliott J, Oakley G G. NBS1 mediates ATR-dependent RPA hyperphosphorylation following replication-fork stall and collapse. J Cell Sci 2007 Dec. 1; 120(Pt 23): 4221-9.

(29) Baldwin E L, Osheroff N. Etoposide, topoisomerase II and cancer. Curr Med Chem Anticancer Agents 2005 July; 5(4):363-72.

(30) Ishimi Y, Sugasawa K, Hanaoka F, Eki T, Hurwitz J. Topoisomerase II plays an essential role as a swivelase in the late stage of SV40 chromosome replication in vitro. J Biol Chem 1992; 267(1):462-6.

(31) Perrault R, Cheong N, Wang H C, Wang H Y, Iliakis G. RPA facilitates rejoining of DNA double-strand breaks in an in vitro assay utilizing genomic DNA as substrate. Int J Radiat Biol 2001; 77(5):593-607.

(32) Wang X, Haber J E. Role of *Saccharomyces* single-stranded DNA-binding protein RPA in the strand invasion step of double-strand break repair. PLoS Biol 2004 January; 2(1):E21.

(33) Stauffer M E, Chazin W J. Physical interaction between replication protein A and Rad51 promotes exchange on single-stranded DNA. J Biol Chem 2004 Jun. 11; 279 (24):25638-45.

We claim:

1. A method of treating ovarian cancer in a subject in need of such treatment comprising a. administering a compound of the formula

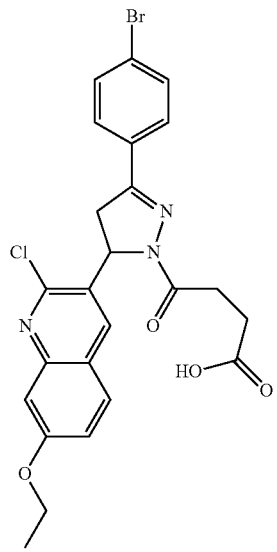 [SMILES: CCOc1ccc2cc(C3CC(c4ccc(Br)cc4)=NN3C(=O)CCC(=O)O)c(Cl)nc2c1]

or

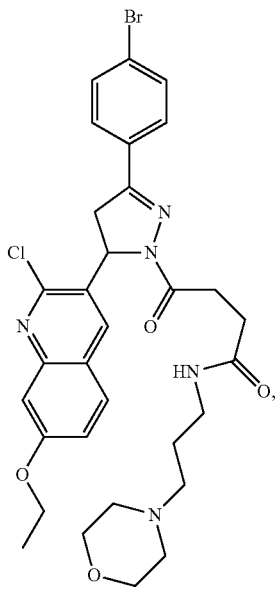 [SMILES: CCOc1ccc2cc(C3CC(c4ccc(Br)cc4)=NN3C(=O)CCC(=O)NCCCN3CCOCC3)c(Cl)nc2c1]

or a pharmaceutically acceptable salt thereof, wherein the compound, or a metabolite thereof, binds to Replication Protein A.

2. The method according to claim 1, wherein the compound is of the formula

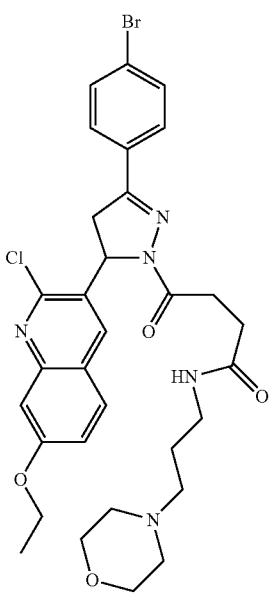 [SMILES: CCOc1ccc2cc(C3CC(c4ccc(Br)cc4)=NN3C(=O)CCC(=O)NCCCN3CCOCC3)c(Cl)nc2c1]

or a pharmaceutically acceptable salt thereof or a metabolite thereof.

3. The method according to claim 1, wherein the compound is of the formula

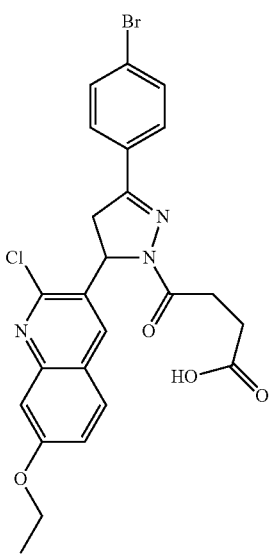 [SMILES: CCOc1ccc2cc(C3CC(c4ccc(Br)cc4)=NN3C(=O)CCC(=O)O)c(Cl)nc2c1]

or a pharmaceutically acceptable salt thereof or a metabolite thereof.

4. The method according to claim 1, wherein the compound is suitable for oral administration.

5. The method according to claim 1, wherein the compound is in a formulation comprising methylcellulose.

6. The method according to claim 1, wherein the compound is suitable for intraperitoneal administration.

7. The method according to claim 1, wherein the compound is in a formulation comprising Tween-80.

8. The method of claim 1, wherein the subject is an animal.

9. The method of claim 1, wherein the subject is a human patient.

10. The method according to claim 9, wherein the compound is administered in a dose of about 50 mg of said compound per kg of the human patient's body weight.

11. The method according to claim 9, wherein the compound is administered in a dose of about 100 mg of said compound per kg of the human patient's body weight.

12. The method according to claim 9, wherein the compound is administered in a dose of about 200 mg of said compound per kg of the human patient's body weight.

13. A method of treating ovarian cancer in a subject in need of such treatment comprising a. administering a compound of the formula

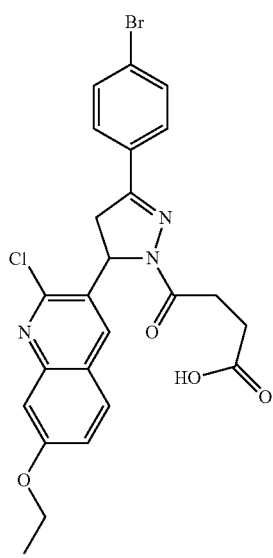 [SMILES: CCOc1ccc2cc(C3CC(c4ccc(Br)cc4)=NN3C(=O)CCC(=O)O)c(Cl)nc2c1]

or

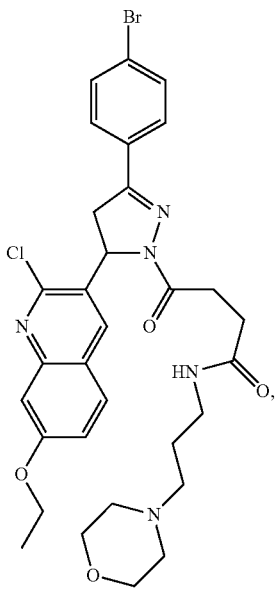 [SMILES: CCOc1ccc2cc(C3CC(c4ccc(Br)cc4)=NN3C(=O)CCC(=O)NCCCN3CCOCC3)c(Cl)nc2c1]

or a pharmaceutically acceptable salt thereof, wherein the compound, or a metabolite thereof, binds to Replication Protein A; and b. administering to the subject a therapeutically effective amount of at least one compound that is a chemotherapeutic DNA damaging agent or a topoisomerase II inhibitor.

14. The method according to claim 13, wherein the compound that binds to Replication Protein A is of the formula

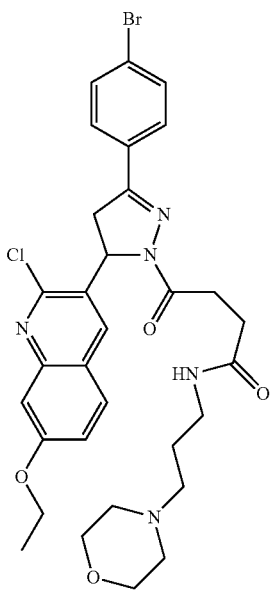 [SMILES: CCOc1ccc2cc(C3CC(c4ccc(Br)cc4)=NN3C(=O)CCC(=O)NCCCN3CCOCC3)c(Cl)nc2c1]

or a pharmaceutically acceptable salt thereof or a metabolite thereof.

15. The method according to claim 13, wherein the compound that binds to Replication Protein A is of the formula

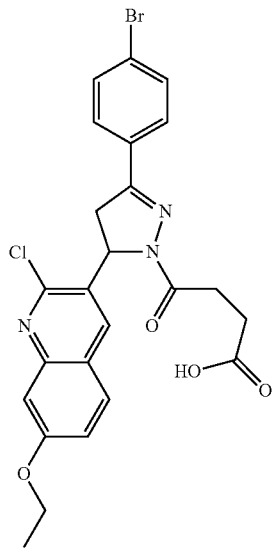 [SMILES: CCOc1ccc2cc(C3CC(c4ccc(Br)cc4)=NN3C(=O)CCC(=O)O)c(Cl)nc2c1]

or a pharmaceutically acceptable salt thereof or a metabolite thereof.

16. The method according to claim 13, wherein the chemotherapeutic DNA damaging agent is selected from the group consisting of: Cisplatin, Etoposide, Busulfan, Bendamustine, Carboplatin, Carmustine, Chlorambucil, Cyclophosphamide, Dacarbazine, Daunorubicin, Decitabine, Doxorubicin, Epirubicin, Etoposide, Idarubicin, Ifosfamide, Irinotecan, Lomustine, Mechlorethamine, Melphalan, Mitomycin C, Mitoxantrone, Oxaliplatin, Temozolomide, and Topotecan.

17. The method according to claim 13, wherein the chemotherapeutic DNA damaging agent is Cisplatin, Etoposide, or a combination thereof.

18. The method according to claim 13, wherein the compound that binds to Replication Protein A is suitable for oral administration.

19. The method according to claim 13, wherein the compound that binds to Replication Protein A is in a formulation comprising methylcellulose.

20. The method of claim 13, wherein the subject is a human patient.

* * * * *